US010918424B2

(12) United States Patent
Stoll et al.

(10) Patent No.: US 10,918,424 B2
(45) Date of Patent: Feb. 16, 2021

(54) ROD REDUCER RATCHET LOCK-OUT MECHANISM

(71) Applicant: Zimmer Biomet Spine, Inc., Westminster, CO (US)

(72) Inventors: Caleb Lee Stoll, Broomfield, CO (US); Allison Christine Capote, Boulder, CO (US); Randall G. Mast, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 16/295,183

(22) Filed: Mar. 7, 2019

(65) Prior Publication Data

US 2019/0274740 A1 Sep. 12, 2019

Related U.S. Application Data

(60) Provisional application No. 62/641,500, filed on Mar. 12, 2018.

(51) Int. Cl.
*A61B 17/70* (2006.01)
*A61B 90/00* (2016.01)
*A61B 17/00* (2006.01)

(52) U.S. Cl.
CPC ...... *A61B 17/7086* (2013.01); *A61B 17/7091* (2013.01); *A61B 90/03* (2016.02); *A61B 2017/00407* (2013.01)

(58) Field of Classification Search
CPC .................................................. A61B 17/7086
See application file for complete search history.

(56) References Cited

U.S. PATENT DOCUMENTS 10,085,778 B2 * 10/2018 Semingson ........ A61B 17/7085
10,136,927 B1 * 11/2018 Lish .................. A61B 17/7086
(Continued)

FOREIGN PATENT DOCUMENTS

| CN | 110251221 A | 9/2019 |
| JP | 2011514830 A | 5/2011 |
| JP | 2019177138 A | 10/2019 |

OTHER PUBLICATIONS

"European Application Serial No. 19162309.9, Extended European Search Report dated Jul. 19, 2019", 10 pgs.
(Continued)

*Primary Examiner* — Jan Christopher L Merene
(74) *Attorney, Agent, or Firm* — Schwegman Lundberg & Woessner, P.A.

(57) ABSTRACT

Spinal surgical procedures can benefit from a rod reduction instrument with a ratchet lock-out mechanism. The instrument can include an inner shaft, an outer housing and a ratchet mechanism. The inner shaft can include a threaded proximal portion and a distal end that includes a plurality of engagement members adapted to receive a pedicle screw. The outer housing can be slidably received over the inner shaft, and include a top sleeve and a bottom sleeve. The top sleeve can include the ratchet mechanism to selectively engage the threaded proximal portion of the inner shaft and the bottom sleeve can engage a connecting rod. The ratchet mechanism can include an engagement feature to selectively engage the threaded proximal portion of the inner shaft, and a locking mechanism to selectively lock the engagement feature of the ratchet mechanism against the threaded proximal portion of the inner shaft.

20 Claims, 13 Drawing Sheets

(56) References Cited

U.S. PATENT DOCUMENTS

| | | |
|---|---|---|
| 2007/0213714 A1 | 9/2007 | Justis |
| 2008/0243190 A1 | 10/2008 | Dziedzic et al. |
| 2012/0191144 A1* | 7/2012 | Peultier .............. A61B 17/7086 606/86 A |
| 2012/0283786 A1 | 11/2012 | Rezach et al. |
| 2014/0316475 A1 | 10/2014 | Parikh et al. |
| 2015/0051648 A1* | 2/2015 | May ................... A61B 17/7086 606/264 |
| 2015/0066042 A1* | 3/2015 | Cummins .......... A61B 17/7091 606/104 |
| 2015/0142067 A1 | 5/2015 | Bess et al. |
| 2016/0030093 A1 | 2/2016 | Walker |
| 2016/0106480 A1 | 4/2016 | Zhou et al. |
| 2017/0252074 A1 | 9/2017 | Semingson et al. |

OTHER PUBLICATIONS

"European Application Serial No. 19162309.9, Response filed Mar. 18, 2020 to Extended European Search Report dated Jul. 19, 2019", 15 pgs.

"Japanese Application Serial No. 2019-043572, Notification of Reasons for Rejection dated Jun. 5, 2020", (W/ English Translation), 5 pgs.

"Japanese Application Serial No. 2019-043572, Response filed Aug. 13, 2020 to Notification of Reasons for Rejection dated Jun. 5, 2020", with English claims, 10 pages.

\* cited by examiner

ROD REDUCER RATCHET LOCK-OUT MECHANISM

CLAIM OF PRIORITY

This application claims the benefit of U.S. Provisional Patent Application Ser. No. 62/641,500, filed on Mar. 12, 2018, the benefit of priority of which is claimed hereby, and which is incorporated by reference herein in its entirety.

TECHNICAL FIELD

The present application relates to spinal fusion procedures involving use of rod reduction instruments to assist in securing connecting rods in pedicle screw implants to immobilize one or more vertebrae.

BACKGROUND

A common surgical procedure to correct deformities in the spine involves stabilizing affected vertebral bodies with interbody implants, pedicle screws and connecting rods. The interbody implants are used to replace disc material between the affected vertebral bodies, and promote honey fusion between the vertebrae. The pedicle screws and connecting rods are used to stabilize the affected portion of the spine to allow fusion to occur. The portion of the procedure involving rod reduction instruments involves implanting pedicle screws bilaterally in affected vertebral bodies and then connecting the pedicle screw implants with stiff, usually metal, connecting rods to secure the vertebrae in a desired orientation. Often a surgeon is attempting to restore some sort of natural curvature or realign a displaced vertebra (spondylosis) It is not uncommon during these procedures for a surgeon to utilize an instrument designed to assist in leveraging a connecting rod into a pedicle screw to restore alignment, these instruments are commonly referred to as rod reduction instruments. Rod reduction may be necessary due to curvature correction or the degree of misalignment (e.g., to pull a vertebra back into alignment).

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The instrument discussed below can be used to quickly and efficiently reduce connecting rods during spinal fusion procedures utilizing pedicle screws and connecting rods. The inventors have recognized that spinal surgeons need rod reduction instruments that can quickly engage connecting rods, provide mechanical advantage when needed, and have mechanical mechanisms to ensure ease of removal at completion of the procedure. Rod reduction instruments can utilize threaded shafts to provide mechanical advantage to reduce connecting rods through rotation of an instrument handle, such as a t-handle. However, reduction instruments that solely utilize threaded reduction can slow down spinal procedures and require too much manipulation to first engage the rod. Ratchet mechanisms can be utilized to reduce the time and effort to make initial engagement of a connecting rod, but ratchet mechanisms can jam during use and cause difficulties in completing a procedure. In extreme cases, jammed instruments can require cutting the connecting rod and removing the pedicle screw. The current inventors have developed various ratchet lock-out mechanisms for use in rod reduction instruments to solve the problem of jammed instruments and still provide all the benefits of instruments with ratcheting capabilities.

Rod reduction instruments are typically provided as part of a fixation system that includes implants (pedicle screws), various length connecting rods, and various instruments for the procedure. The instruments can include tools for pedicle targeting, pedicle preparation, screw insertion, rod and closure top insertion, and manipulation. Manipulation tools include rod reduction instruments, such as rod rockers and reducers. The instruments discussed herein are variations of axial reducers, but the ratchet lock-out mechanisms and techniques could be implemented on other rod reduction instruments utilizing a threaded shaft. Commercial examples of axial reducers include reduction instruments provided by Zimmer Biomet as part of the Vital™ Spinal Fixation System. Commercial examples of rocket reducers include reducers provided by Zimmer Biomet as part of the Polaris™ or Lineum™ OCT spinal deformity correction systems. Surgical technique guides from Zimmer Biomet, for systems such as the Vital™ Spinal Fixation System, provide an excellent overview of reduction instrument use and interactions with pedicle screw implants and connecting rods. Accordingly, details regarding how these instruments connect with the implants and operate are not discussed in detail, accept as needed to under the inventive concepts discussed herein.

Figure 1A:
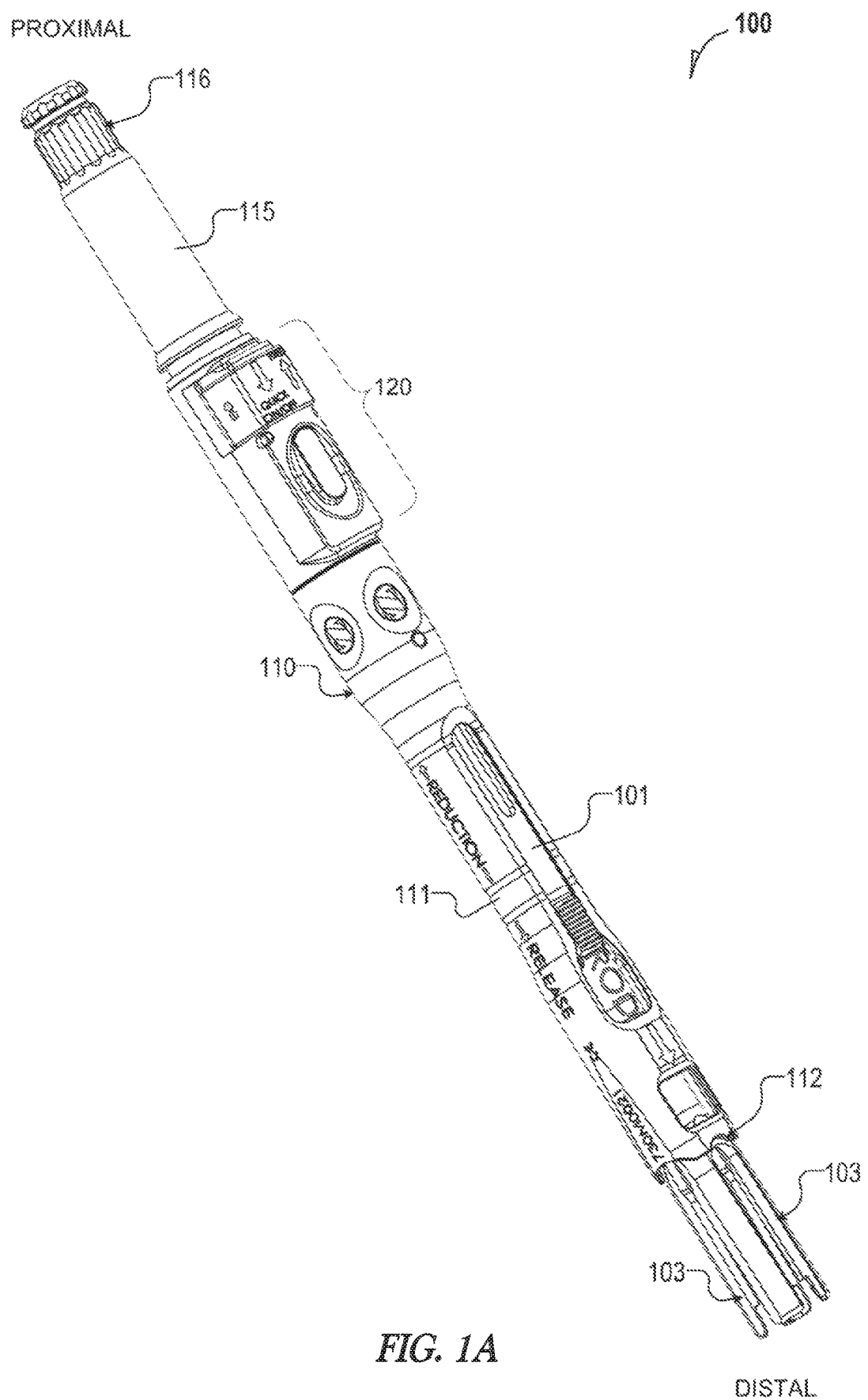
FIG. 1A is an isometric view of a rod reduction instrument, in accordance with an example embodiment.

FIG. 1A is an isometric view of a rod reduction instrument 100, in accordance with an example embodiment. Rod reduction instrument 100 can include inner sleeve 101 and outer housing 110. The distal end of the inner sleeve 101 can include engagement members 103, which are adapted to engage a housing on a pedicle screw that receives a connecting rod. The outer housing 110 can include a top sleeve 115 rotationally coupled to a bottom sleeve 111. The top sleeve 115 can include a tool socket 116 and a ratchet mechanism 120. The distal end of the bottom sleeve 111 can include a rod engagement 112, which in this example is a semi-circular cutout in opposing sides of the distal end. In operation, the outer housing 110 translates over the inner shaft 101, after the inner shaft 101 is coupled to the pedicle screw head via engagement members 103.

The rod reduction instrument 100 is an example of a tower reducer that incorporates the ratchet lock-out mechanism to enable two different reduction modes of operation. First, with the ratchet mechanism operation, the tower reducer operates in a quick on, quick off mode that captures the screw head and engages the rod more quickly. After coupling the engagement members 103 of the inner sleeve 101 to a head of a pedicle screw, the outer housing 110 can slide over the inner sleeve 101 until the rod engagement 112 engages the rod. A T-handle or similar tool can then be attached to the tool socket 116 to rotate the top sleeve 115 causing the outer housing 110 to translate further downward reducing the rod into the head of the pedicle screw. Threaded reduction using the tool socket 116 is accomplished by an engagement feature of the ratchet mechanism 120 engaging a threaded proximal portion of the inner sleeve 101. In an example, the engagement feature can be a threaded portion of the ratchet mechanism 120. In other examples, the engagement feature can be an alternative structure, such as small protrusions (numbs) or captured ball bearings.

The ratchet mechanism, discussed in greater detail below, can be temporarily disengaged through activation of a button, which allows smooth and quick initial engagement of the connecting rod. In same examples, the button on the ratchet mechanism 120 needs to be activated to allow the outer housing 110 to freely translate over the inner sleeve 101. In other examples, the ratchet mechanism 120 allows the engagement feature of skip over the threads on the proximal section of the inner sleeve 101 without activation of the button on the ratchet mechanism.

In this example, the ratchet mechanism 120 can be shifted into a fixed or threaded mode of operation, locking out the ratchet mechanism. As discussed in detail below, locking out the ratchet mechanism involves forcing an engagement feature of the ratchet mechanism into fixed engagement with a threaded portion of the inner sleeve 101. In this fixed mode, the reducer operates as a threaded reduction instrument, with no rapid translation of the outer housing 110. Accordingly, in the fixed mode the outer housing 110 translates based solely on rotation input received through the tool socket 116 (or any rotation of the top sleeve 115 portion of the outer housing 110). Shifting the ratchet mechanism 120 of the reduction instrument 100 into fixed mode enables a user to remove the reduction instrument from difficult reduction scenarios, where a ratcheting reduction instrument may not function properly due to high reduction forces. For example, because ratcheting instruments typically rely upon some form of biasing element, such as a coil spring, to keep a threaded member engaged with the threaded inner sleeve, in certain situations the coils spring can fail to keep the threads engaged sufficiently to overcome forces operating on the instrument. In these situations, a ratcheting only instrument may have to be removed through extraordinary measures, such as cutting the connecting rod and removing the pedicle screw. A dual mode ratcheting mechanism with a lock-out capability can avoid such extraordinary measures by providing a mechanism to fix engagement of the engagement feature of the ratchet against the threaded portion of the inner sleeve. In the fixed engagement mode, the reduction instrument can leverage the mechanical advantage of the threads to overcome external forces jamming the instrument.

Figure 1B:
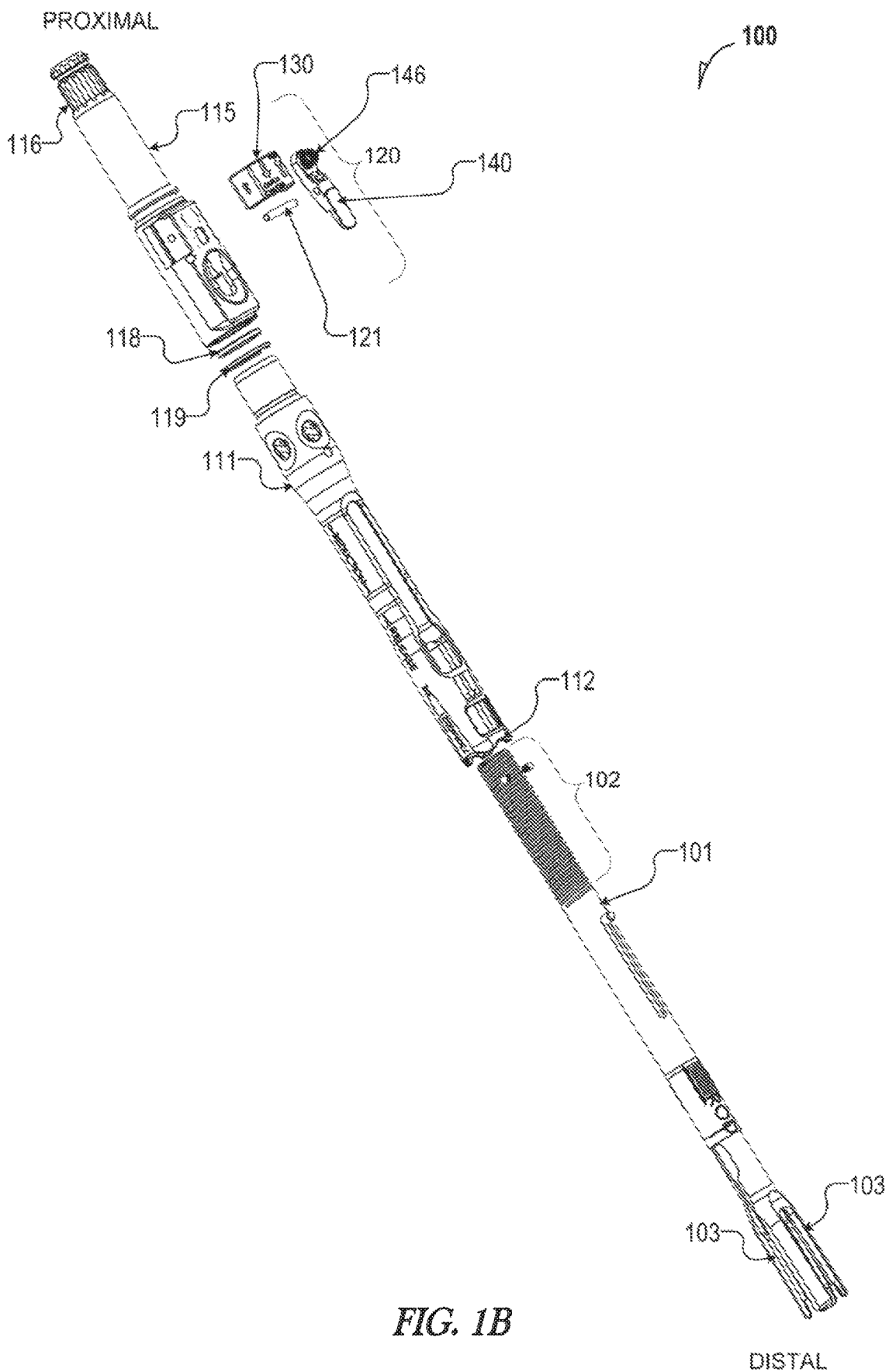
FIG. 1B is an exploded isometric view of a rod reduction instrument, in accordance with an example embodiment.

FIG. 1B is an exploded isometric view of the rod reduction instrument 100 introduced above. The exploded view provides an introduction to additional elements of an example ratcheting mechanism as well as the overall instrument in accordance with this example. The rod reduction instrument 100 can include an inner sleeve 101, a threaded proximal portion 102 of the inner sleeve 101, and a plurality of engagement members 103 (collectively referenced as engagement members 103). The rod reduction instrument 100 can also include an outer housing that includes a top sleeve 115 that rotates in reference to a bottom sleeve 111. The top sleeve 115 is coupled to the bottom sleeve via a thrust washer 118 and retaining ring 119. In this example, the ratchet mechanism 120 can include a pivot shaft 121, a locking mechanism 130, a lever member 140, and a biasing member 146.

Figure 2:
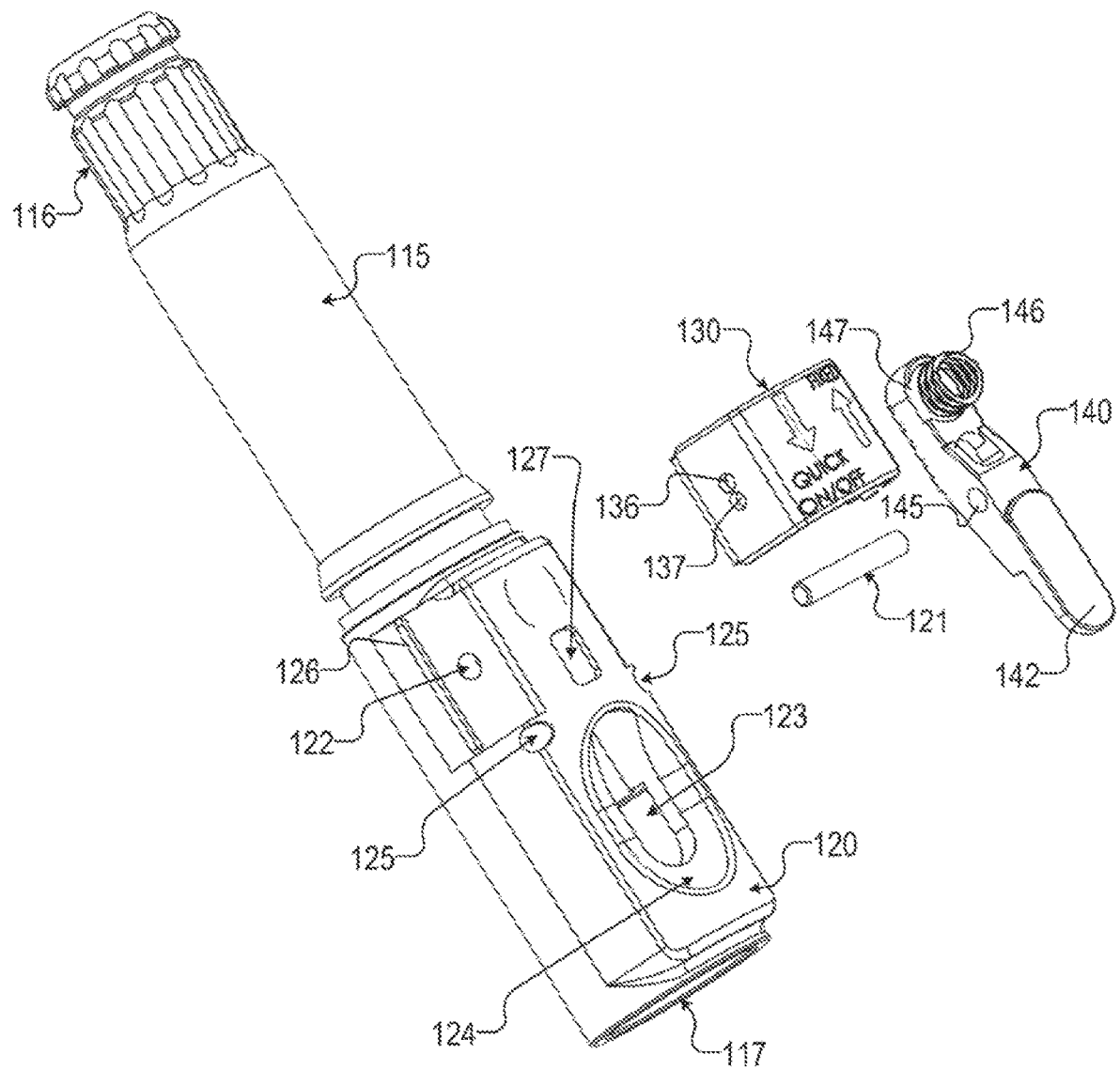
FIG. 2 is an exploded isometric view of an upper section of a rod reduction instrument, in accordance with an example embodiment.

FIG. 2 is an exploded isometric view of an upper section of a rod reduction instrument 100, in accordance with an example embodiment. In this example, the top sleeve 115 and the ratchet mechanism 120 of the rod reduction instrument 100 are illustrated in additional detail. The ratchet mechanism 120 includes features built into the top sleeve 115, such as a detent bore 122, a button opening 123, a button cutout 124, pivot shaft bores 125, slide lock rails 126, and a transverse shaft opening 127. FIG. 2 also illustrates the top sleeve 115 with a tool socket 116 and rotational coupling 117. The rotational coupling 117 is where the top sleeve 115 is connected to the bottom sleeve 111. The ratchet mechanism 120 also includes a pivot shaft 121, a locking mechanism 130, a lever member 140, and a biasing member 146. The locking mechanism 130 can also include a lock detent 136 and a ratchet detent 137, which operate to retain the locking mechanism 130 is one of the two modes (locked or fixed and ratcheting). The lever member 140 can include a ratchet release button 142, a pivot 145, and a bias recess 147. The pivot 145 can receive the pivot shaft 121, and is where the lever member 140 rotates or pivots in ratcheting mode. The biasing member 146 operates to bias the lever member 140 into engagement with the threaded proximal portion of the inner sleeve 101. As illustrated in greater detail in FIGS. 3A-3J, the biasing member 146 can be a wave washer spring, but can also be a coil spring or other comparable biasing member. In certain examples, an elastic or elastomeric material could be substituted for the wave washer spring. The biasing member needs to allow for sufficient travel to clear threaded on the inner shaft, with provide a balance between thread engagement and ratcheting motion.

The locking mechanism 130 slides on the slide lock rails 126 when assembled into the ratchet mechanism 120. The detent bore 122 is designed to hold a detent ball to engage the lock detent 136 and ratchet detect 137 when locking mechanism 130 slides between fixed mode and ratcheting mode (also referred to as Quick On/Off mode).

Figure 3A:
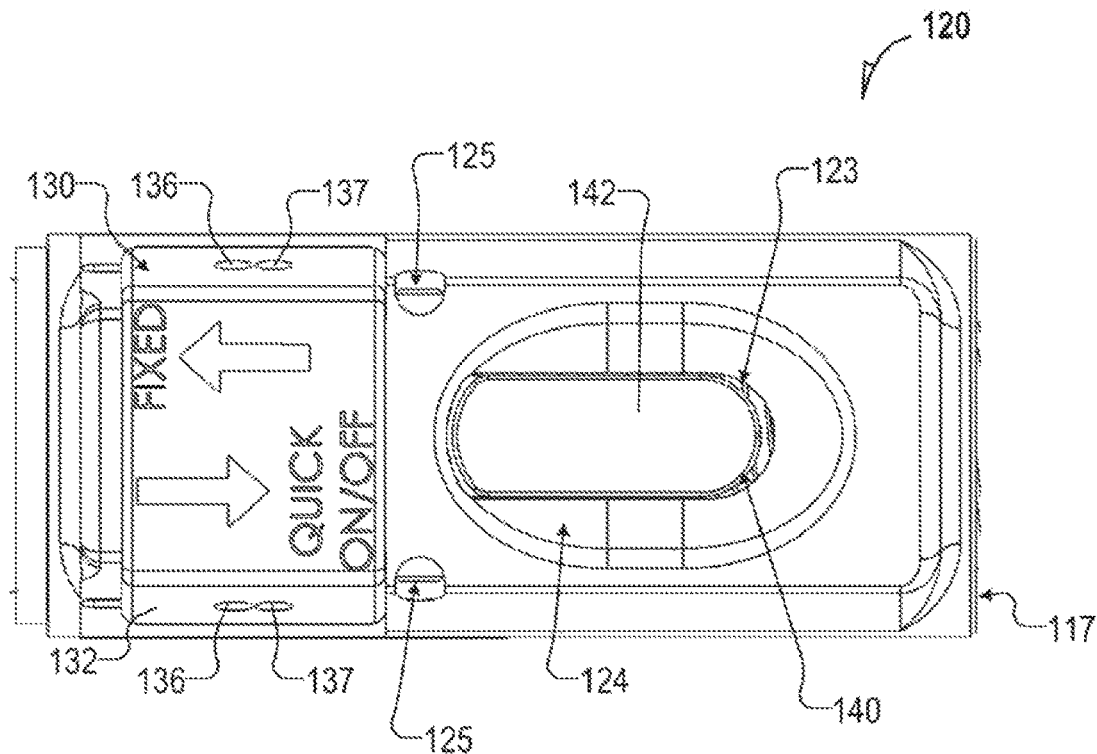
FIGS. 3A-3J are diagrams and drawings of a ratchet mechanism used in a rod reduction instrument, in accordance an example embodiment.

FIGS. 3A-3J are diagrams and drawings of a ratchet mechanism used in a rod reduction instrument, in accordance an example embodiment. FIG. 3A is a drawing of a superior surface of an assembled the ratchet mechanism 120. In this example, the ratchet mechanism 120 can include button opening 123, button cutout 124, pivot shaft bores 125, a locking mechanism 130, lever member 140, and ratchet release button 142. The locking mechanism in this example includes slide lock 132, which is a U-shaped linear slide that is further illustrated in the following figures. In this example, the lock detent 136 and ratchet detent 137 are shown on opposing arms of the U-shaped slide lock 132.

Figure 3B:
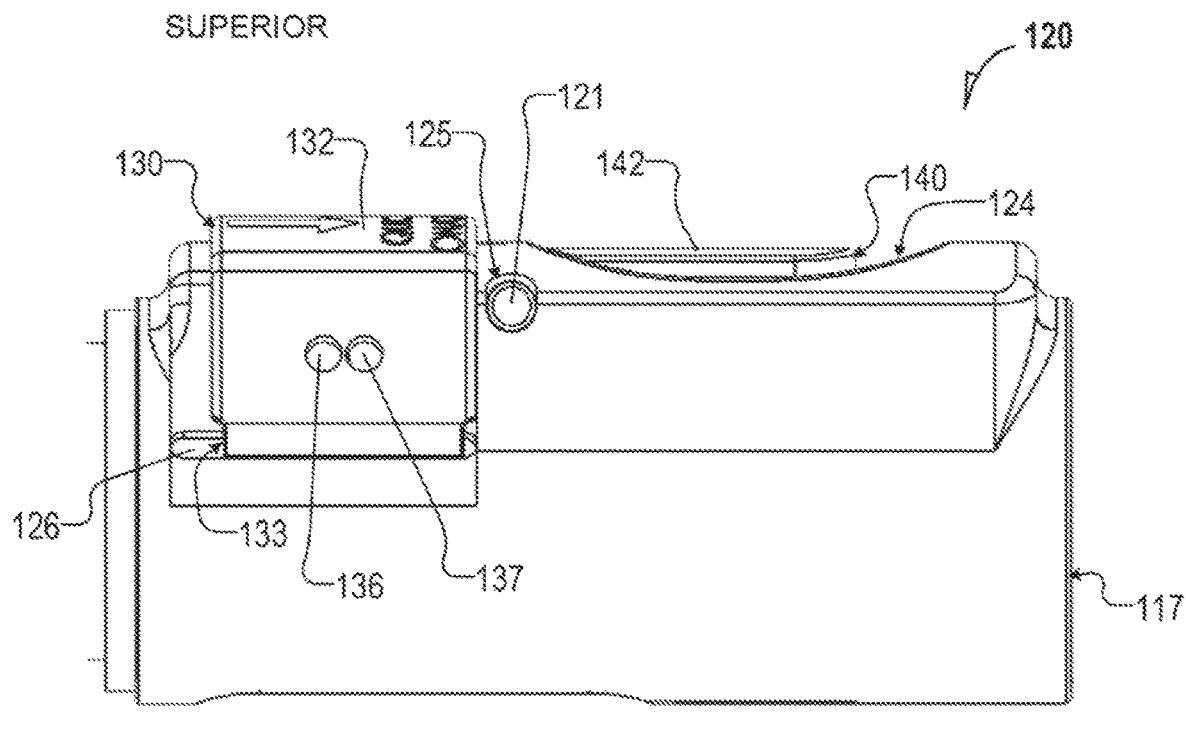

FIG. 3B is a drawing of a lateral side of the ratchet mechanism 120. In this view, the slide lock 132 is illustrated engaged with one of the slide lock rails 126 along a slide recess 133. The slide lock 132 includes a slide recess 133 along the outbound edge of each arm of the U-shaped structure. Also illustrated in this view is the pivot shaft 121 within the pivot shaft bore 125. When the ratchet release button 142 of the lever member 140 is activated, the lever member 140 pivots on the pivot shaft 121 and the engagement feature 141 disengages from an threaded portion of the inner shaft 101.

Figure 3C:
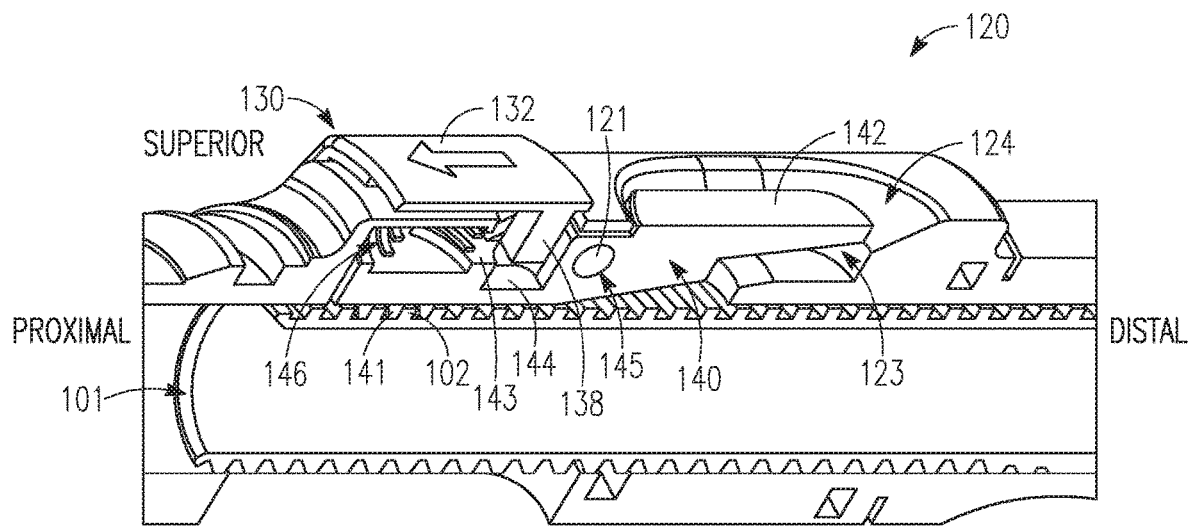
Figure 3D:
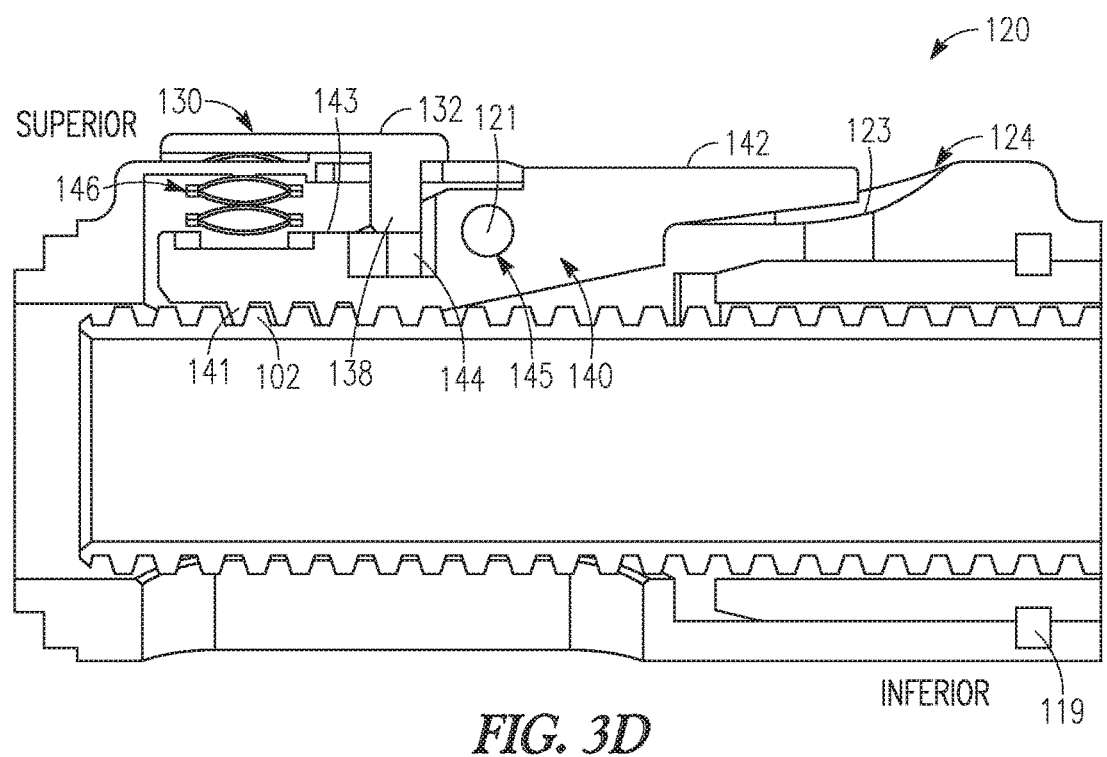

FIGS. 3C-3D are cutaway views of the ratchet mechanism 120 and associated portions of the inner sleeve 101. In these views, the following ratchet mechanism 120 details are depicted, pivot shaft 121, button opening 123, button cutout 124, slide lock 132, lever member 140, and biasing member 146. In this example, the slide lock 132 includes the transverse shaft 138, which is the structure of the locking mechanism 130 that locks out the ratcheting action of the lever member 140. In these views, the lever member 140 is illustrated as including an engagement feature 141 on an inferior side of the proximal portion. The cutaway demonstrates how the engagement feature 141 engages the proximal threaded portion 102 of inner sleeve 101. In this example, the engagement feature 141 is a plurality of partial threads that correspond to the proximal threaded portion 102 of the inner sleeve 101. The cutaway also illustrates how the biasing member 146 biases the engagement feature 141 into engagement with the proximal threaded portion 102. The lever member 140 also includes a locking surface 143 and a ratchet cavity 144, which are positioned below the transverse shaft 138 of the slide lock 132. In ratcheting mode, the slide lock 132 is positioned as shown and the transverse shaft 138 is opposite the ratchet cavity 144, which provides clearance for the lever member 140 to pivot without interference from the transverse shaft 138. However, in the fixed (or locked) mode, the slide lock 132 is shifted proximally, and the transverse shaft 138 is positioned opposite the locking surface 143. In the fixed mode, the lever member 140 is prevented from pivoting due to engagement between the transverse shaft 138 and the locking surface 143.

Figure 3E:
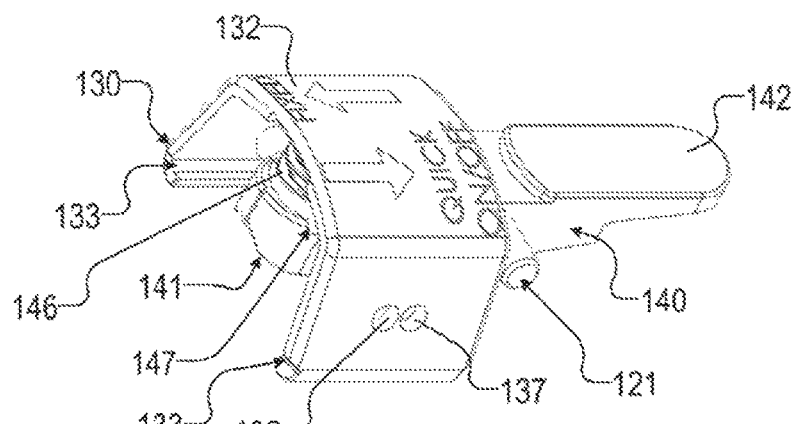
Figure 3F:
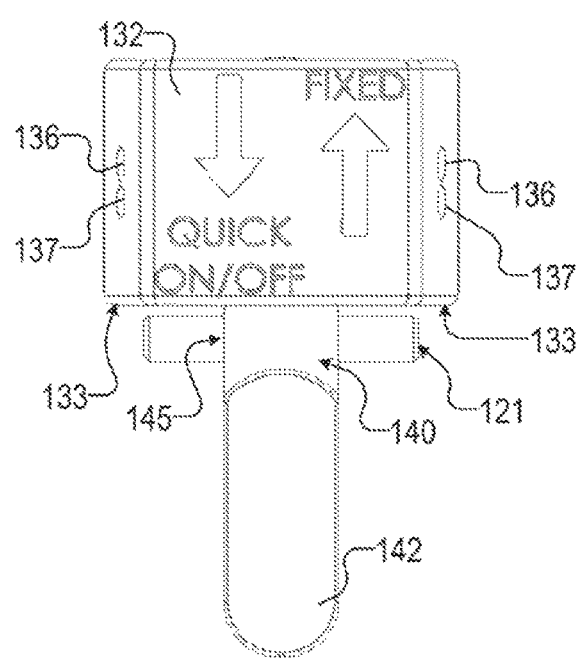
Figure 3G:
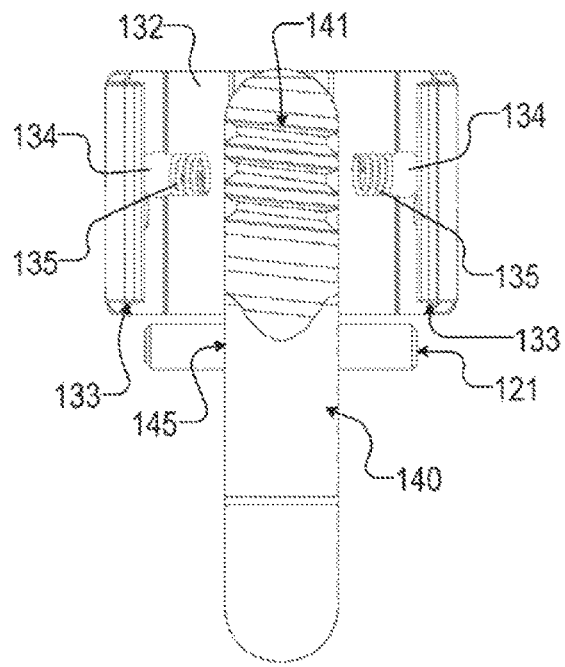
Figure 3H:
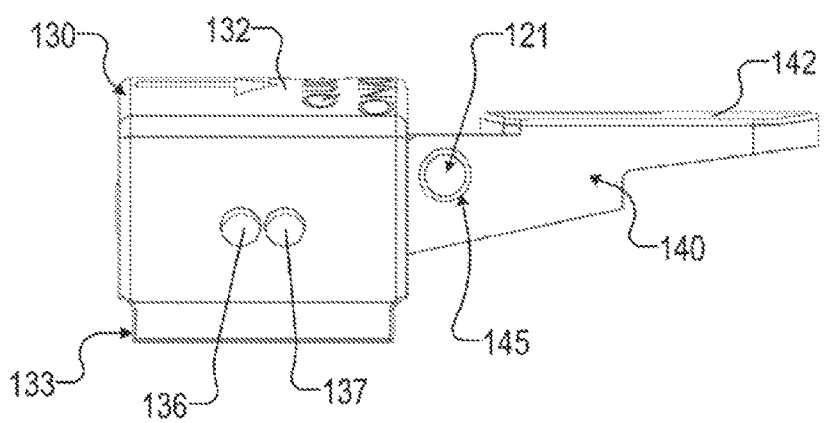
Figure 3I:
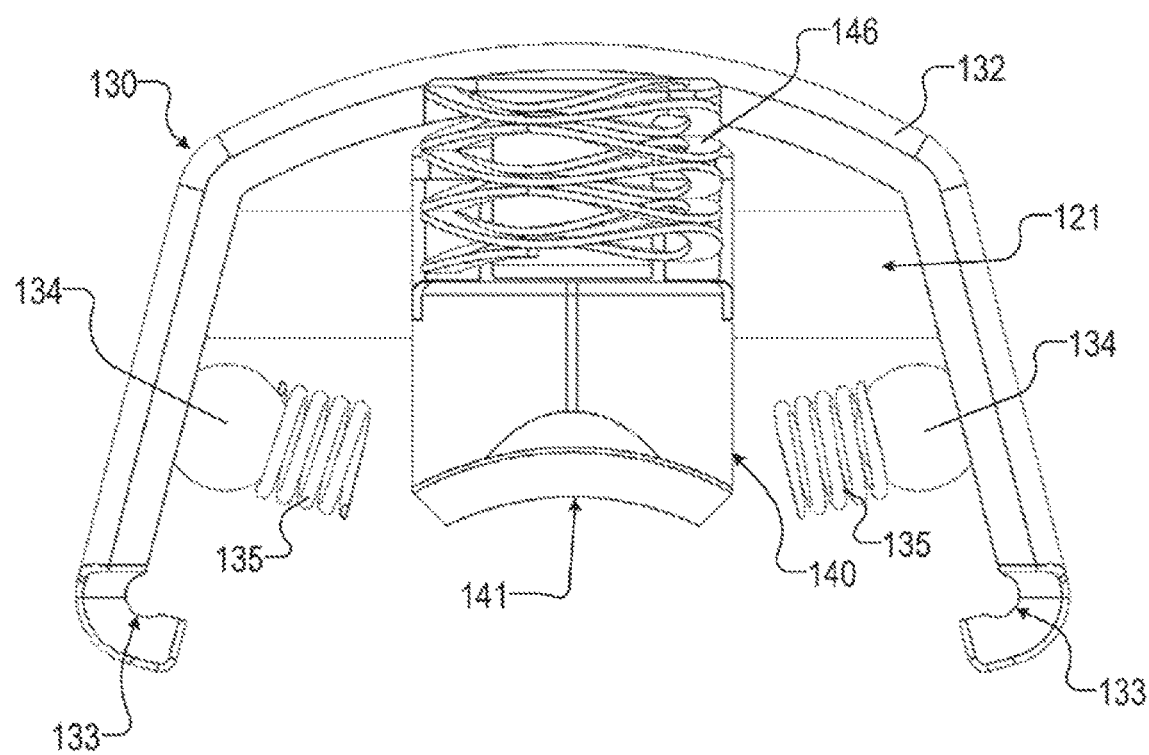
Figure 3J:
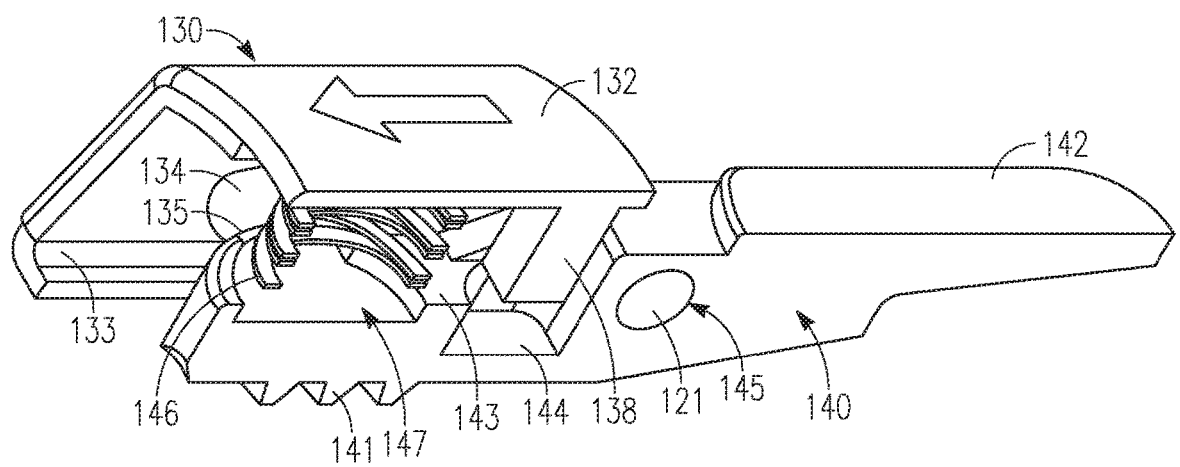

FIGS. 3E-3J are various drawings providing additional detailed views of the locking mechanism 130, the lever member 140, and parts of the ratchet mechanism 120. FIG. 3E is an isometric view of the pivot shaft 121, locking mechanism 130, and lever member 140. In this view, the U-shaped structure of the slide lock 132 is depicted with the slide recesses 133 along the ends of each arm. FIG. 3F is a superior surface view of the locking mechanism 130 and lever member 140. FIG. 3G is an inferior surface view of the locking mechanism 130 and lever member 140. In this view, the engagement feature 141 of the lever member 140 is shown including at least three angled threads in the thread pattern. In other examples, a different thread pattern can be utilized and the engagement feature 141 can have more or fewer threads. In other examples, the engagement feature 141 can include a series of protrusions positioned to engage the threaded proximal portion 102. In yet other examples, the engagement feature 141 can include one or more captured ball bearings positioned to engage the threads in the threaded proximal portion 102, in this example the threads in the threaded proximal portion 102 may be structured to accept the ball bearings. This view also includes detent balls 134 and detent springs 135, which assist in holding slide lock 132 in the fixed or ratcheting position. FIG. 3H is a lateral view drawing of the locking mechanism 130 and lever member 140. FIG. 3I is an axial view along a longitudinal axis of the rod reduction instrument of the locking mechanism 130 and the lever member 140. This view depicts the U-shaped structure of the slide lock 132 with the c-shaped slide recesses 133 on the outbound end of each leg of the U. The view also depicts the curve of the engagement feature 141 on the inferior side of the proximal portion of the lever member 140. Opposite the engagement feature 141 is the biasing member 146, which is held in place by an inferior surface of the slide lock 132. FIG. 3J is a cutaway perspective view of the locking mechanism 130 and lever member 140 providing a slightly different perspective on the elements discussed above.

Figure 4:
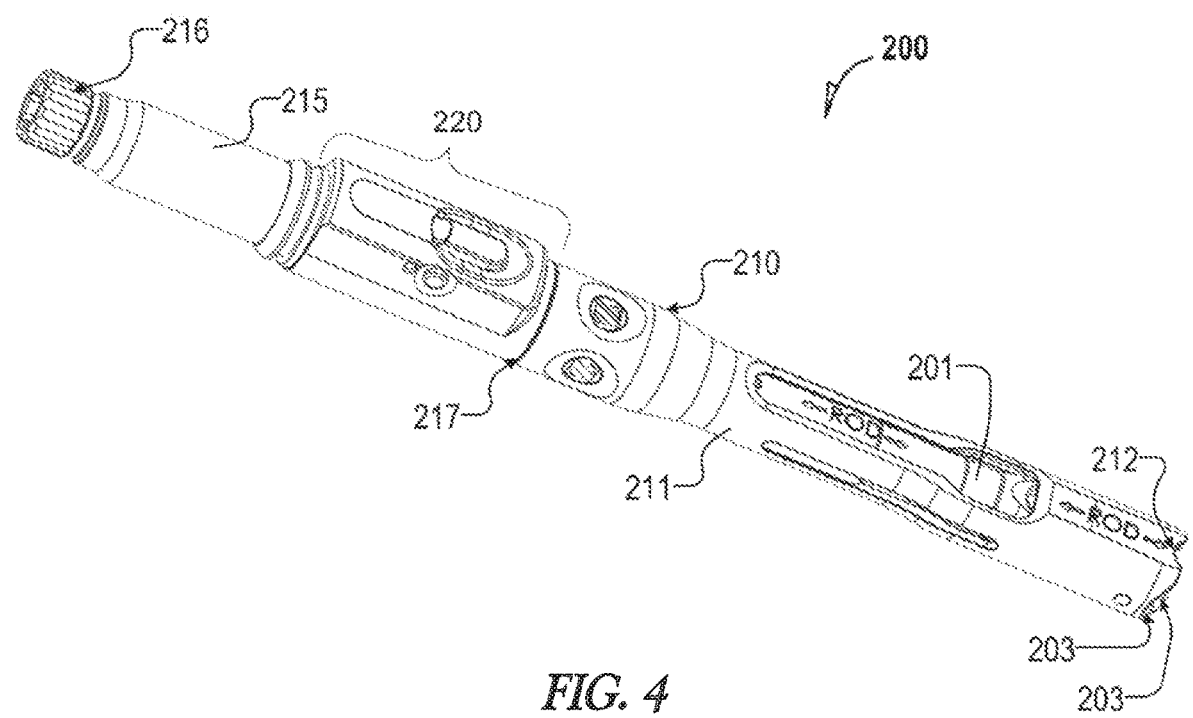
FIG. 4 is an isometric view of a rod reduction instrument, in accordance with an example embodiment.

FIG. 4 is an isometric view of a rod reduction instrument 200, in accordance with an example embodiment. The rod reduction instrument 200 is similar to rod reduction instrument 100 discussed above, but includes a different ratchet lock-out mechanism. The following discussion will primarily focus on the differences in the ratchet mechanism 220, as the rest of the functionality of the rod reduction instrument 200 is comparable to that of rod reduction instrument 100. As illustrated in FIG. 4, the rod reduction instrument 200 can include an inner shaft 201, engagement members 203, an outer housing 210, and a ratchet mechanism 220. The outer housing 210 can include a bottom sleeve 211 and a top sleeve 215. The top sleeve 215 can include a tool socket 216, which can be used to receive a handle to introduce rotation to the top sleeve 215. The top sleeve 215 can rotate in reference to the bottom sleeve 211 around the rotational coupling 217. The bottom sleeve 211 includes a rod engagement 212 on a distal end.

Figure 5:
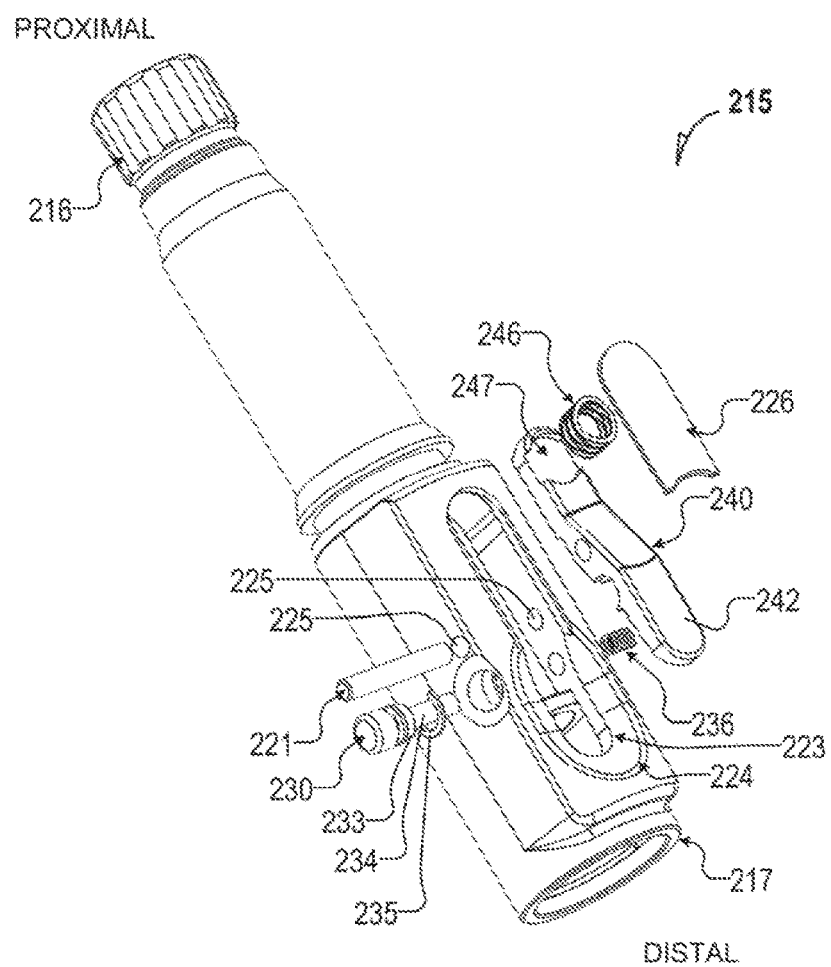
FIG. 5 is an exploded isometric view of an upper section of a rod reduction instrument, in accordance with an example embodiment.

FIG. 5 is an exploded isometric view of an upper section (top sleeve 215) of the rod reduction instrument 200, in accordance with an example embodiment. In this example, the ratchet mechanism 220 includes pivot shaft 221, button opening 223, button cutout 224, pivot shaft bores 225, ratchet cover 226, locking mechanism 230, and lever member 240. The lever member 240 is similar to the lever member 140, and includes a threaded inferior surface on a proximal portion and a ratchet release button 242 on a superior surface of a distal portion. The lever member 240 receives the pivot shaft 221 between the proximal portion and distal portion. On a superior surface of the proximal portion of the lever member 240 there is a bias recess 247 adapted to receive a biasing member 246. In this example, the locking mechanism 230 includes a slide lock 232 in the form of a stepped cylindrical shaft. The slide lock 232 includes a large diameter section 233, a small diameter section 234, a locking ring 235, and a biasing member 236. As assembled, the slide lock 232 is located within a slide lock bore 237 (labeled in FIG. 6J), with the locking ring 235 securing the slide lock 232 shaft within the bore 237.

In this example, the lever member 240 and the biasing member 246 are dropped into the ratchet mechanism 220 through an opening in the superior surface, then the ratchet cover 226 is slid into position over the opening to provide an engagement surface for the biasing member 246 to operate against. In an example, edges of the ratchet cover 226 slide into recesses in the opening in the superior surface of the ratchet mechanism 220. Once the lever member 240 is in position, the pivot shaft 221 can be inserted to retain the lever member 240, while allowing the lever member 240 to pivot.

Figure 6A:
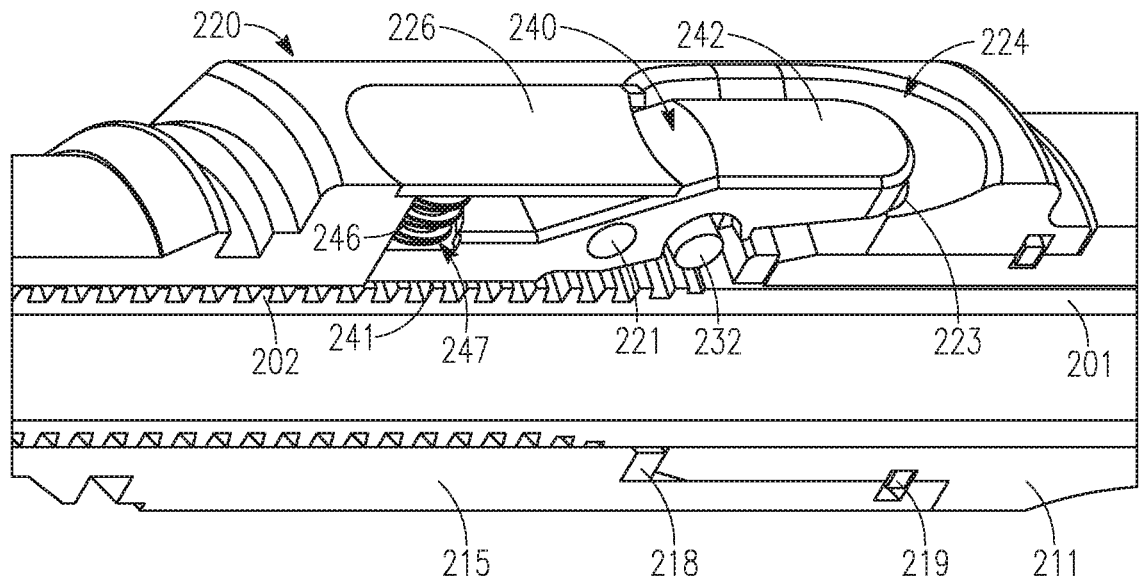
FIGS. 6A-6J are diagrams and drawings of a ratchet mechanism used in a rod reduction instrument, in accordance an example embodiment.
Figure 6B:
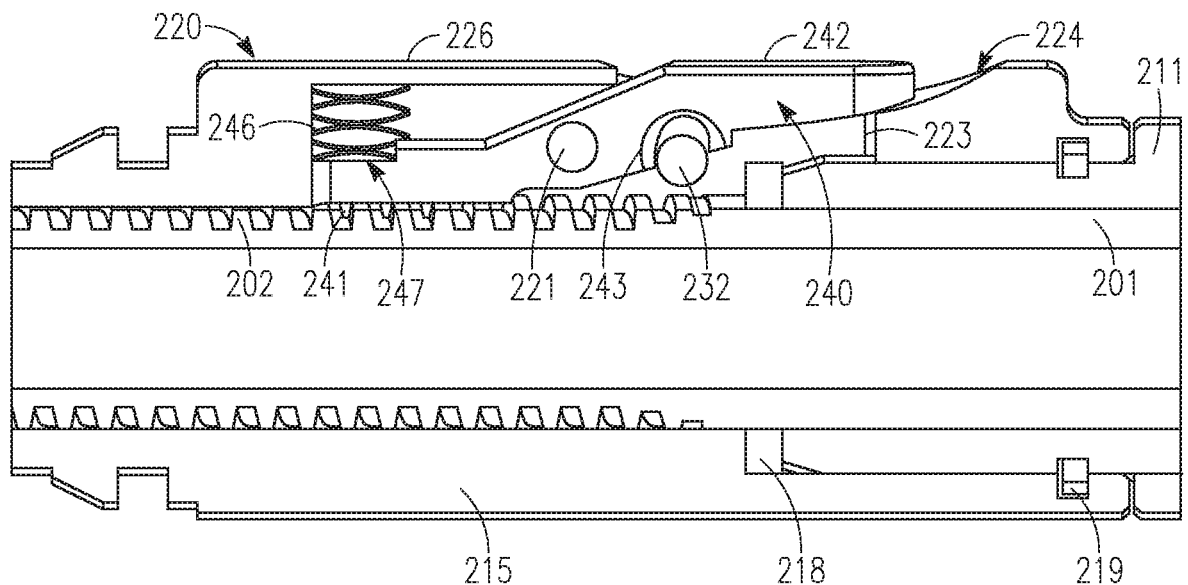

FIGS. 6A-6J are diagrams and drawings of the ratchet mechanism 220 used in a rod reduction instrument 200, in accordance an example embodiment. FIGS. 6A and 6B are cutaway illustrations of the ratchet mechanism 220 as well as depictions of portions of inner shaft 201, top sleeve 215, and bottom sleeve 211. In this example, the thrust washer 218 and retaining ring 219 are illustrated in reference to top sleeve 215 and bottom sleeve 211. Inner shaft 201 includes proximal threaded portion 202, which engages with the engagement feature 241 of the lever member 240. The biasing member 246 is illustrated urging the lever member 240 to pivot on pivot shaft 221 and engage the threaded proximal portion 202 of inner shaft 201. The locking surface 243 is also illustrated in these cutaway views. The locking surface 243 on the lever member 240 is a semi-circular recess along a lateral inferior surface under a portion of the ratchet release button 242. As illustrated in other figures, the large diameter 233 of the slide lock 232 can be shifted laterally into engagement with the locking surface 243 to prevent the lever member 240 from pivoting and forcing the engagement feature 241 into fixed engagement with the threaded proximal portion 202 of inner shaft 201. With the slide lock 232 engaged, the rod reduction instrument 200 operates through rotation of the top sleeve 215 only. The cutaway views also illustrate the structure of the button opening 223 and the button cutout 224. The button opening 223 is an opening in the ratchet mechanism 220 that conforms to the outline of the ratchet release button 242 of the lever member 240, while the button cutout 224 is a recessed portion around the ratchet release button 242. In some examples, the button cutout 224 can include curved sidewalls, and in other examples the sidewalls can be straight but angled.

Figure 6C:
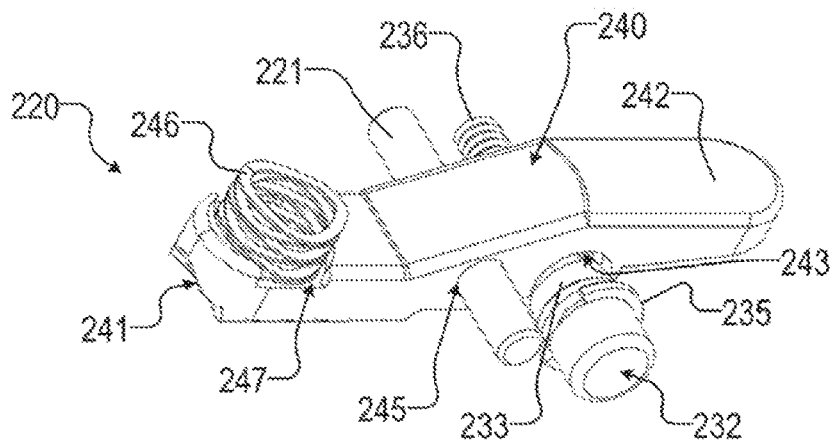

FIG. 6C-6I are various drawings providing additional detailed views of the locking mechanism 230 and lever member 240 parts of the ratchet mechanism 220. FIG. 6C is an isometric view of the pivot shaft 221, locking mechanism 230, and lever member 240. In this example, the pivot 245 of lever member 240 is identified as the bore in the lever member 240 receiving the pivot shaft 221. Other features of the lever member 240 illustrated in this example include engagement feature 241, ratchet release button 242, locking surface 243, bias recess 247, and the bias member 246. This example illustrates the relationship between the locking surface 243 on the lever member 240 and the large diameter section 233 of the stepped cylindrical slide lock 232. While not specifically identified with a reference number, the slide lock 232 includes an enlarged lateral end that operates as a button for activation of the slide lock 232 of the locking mechanism 230.

Figure 6D:
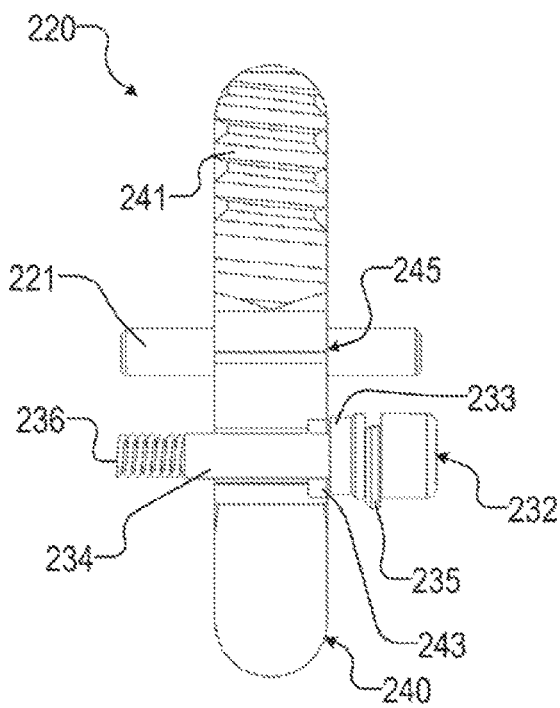

FIG. 6D is an inferior side view of the pivot shaft 221, locking mechanism 230, and lever member 240. In this example, the engagement feature 241 of the lever member 240 is illustrated as including at least three threads running at a shallow angle transverse to a longitudinal axis of the lever member 240. In some example, more or fewer threads can be included on the engagement feature 241. The small diameter section 234 of the slide lock 232 stepped cylindrical shaft is shown within a recess in the inferior side of the ratchet release button 242 portion of the lever member 240. The lock biasing member 236 is illustrated in position to bias the slide lock 232 into an unlocked position.

Figure 6E:
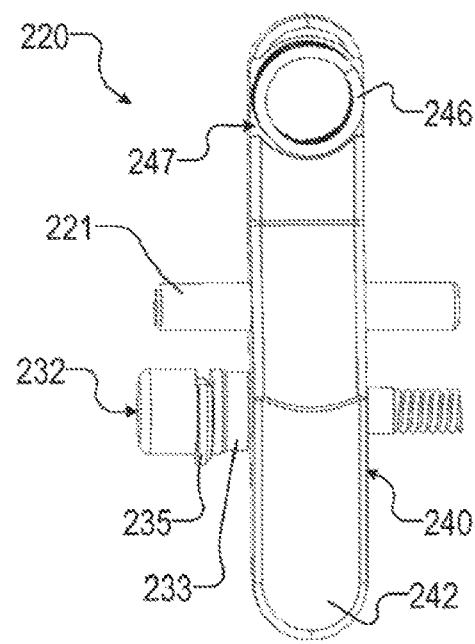
Figure 6F:
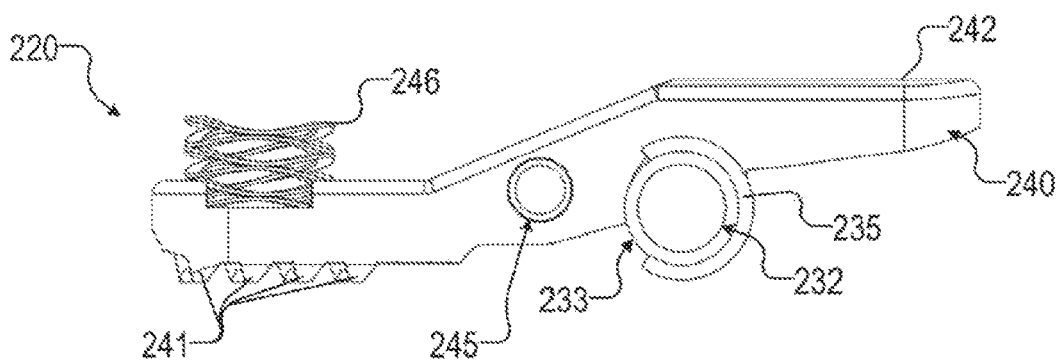

FIG. 6E is a superior side view of the pivot shaft 221, locking mechanism 230, and lever member 240. FIG. 6F is a lateral side view of the pivot shaft 221, locking mechanism 230, and lever member 240. In this view, the engagement feature 241 is illustrated as including four partial threads to engage the threaded proximal portion 202 of the inner shaft 201.

Figure 6G:
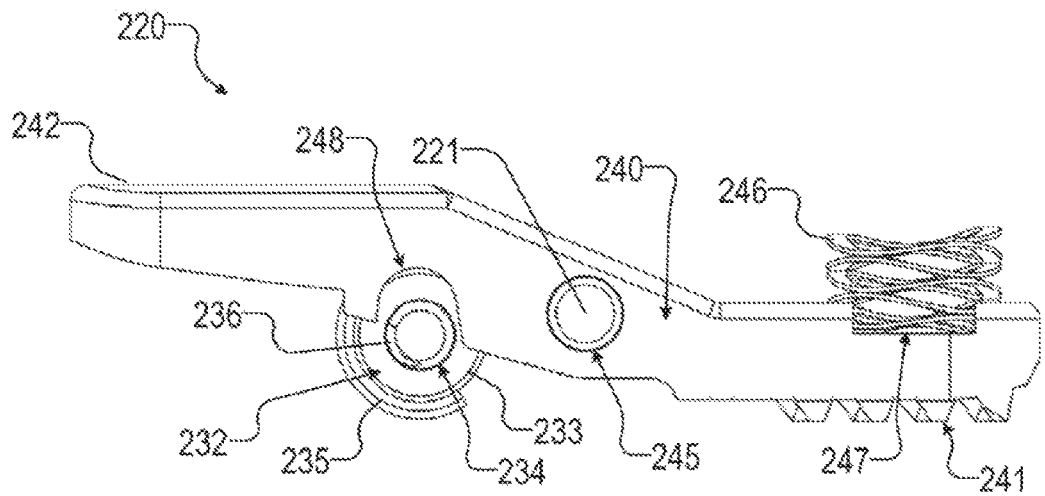
Figure 6H:
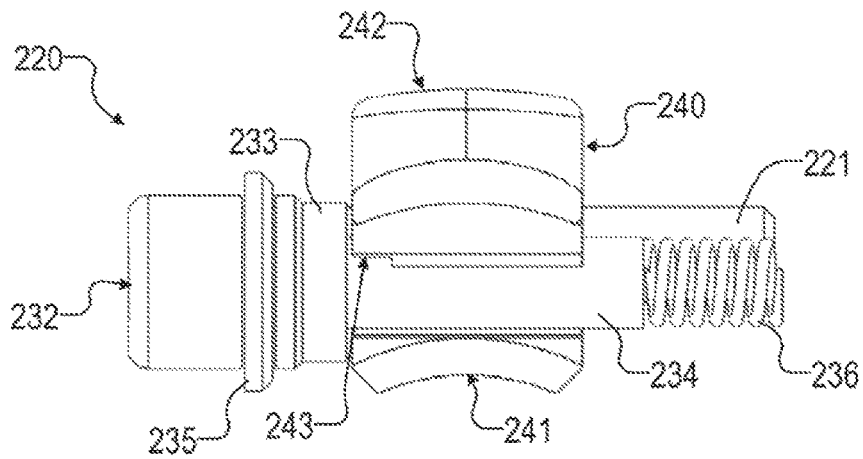
Figure 6I:
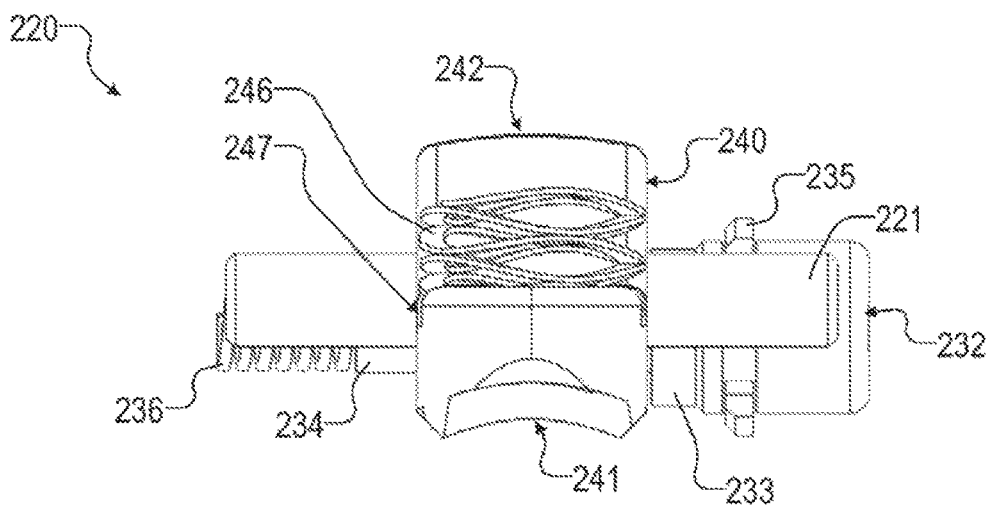

FIG. 6G is a medial side view of the pivot shaft 211, locking mechanism 230, and lever member 240. In this view, the U-shaped slide lock recess 248 in the inferior side of the ratchet release button 242 portion of the lever member 240 is shown in relationship to the small diameter section 234 and lock biasing member 236 of the slide lock 232. The slide lock recess 248 provides sufficient clearance to allow the lever member 240 to pivot around pivot shaft 221 with the ratchet release button 242 is activated, or when ratcheting as the outer housing 210 slides over the inner shaft 201. FIGS. 6G and 6I are distal and proximal views, respectively, along the longitudinal axis of the rod reduction instrument 200. FIG. 6I depicts the curved structure of the inferior surface of the engagement feature 241 of the lever member 240. The engagement feature 241 is curved to match the outer curvature of the inner shaft 201.

Figure 6J:
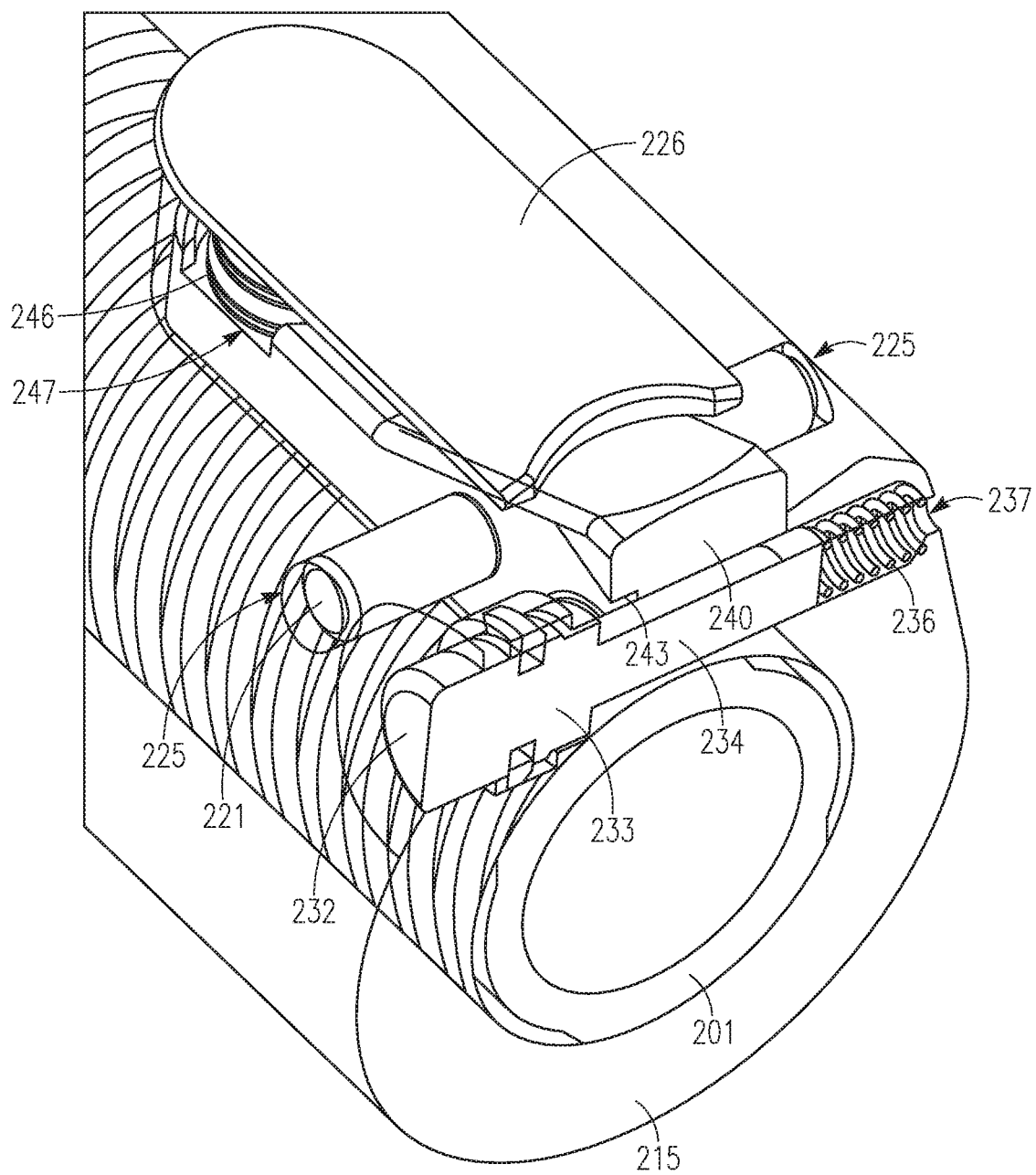

FIG. 6J is a transverse cutaway view of the ratchet mechanism 220, top sleeve 215, and inner shaft 201. The cutway runs through the stepped cylindrical shaft of the slide lock 232. As illustrated, the locking ring 235 retains the slide lock 232 within the slide lock bore 237 by engaging a cylindrical recess enlarging a section of the slide lock bore 237. The cutaway also illustrates how the large diameter section 233 can engage the locking surface 243 on the lever member 240 when the button of the slide lock 232 is pushed in compressing the lock biasing member 236.

Figure 7:
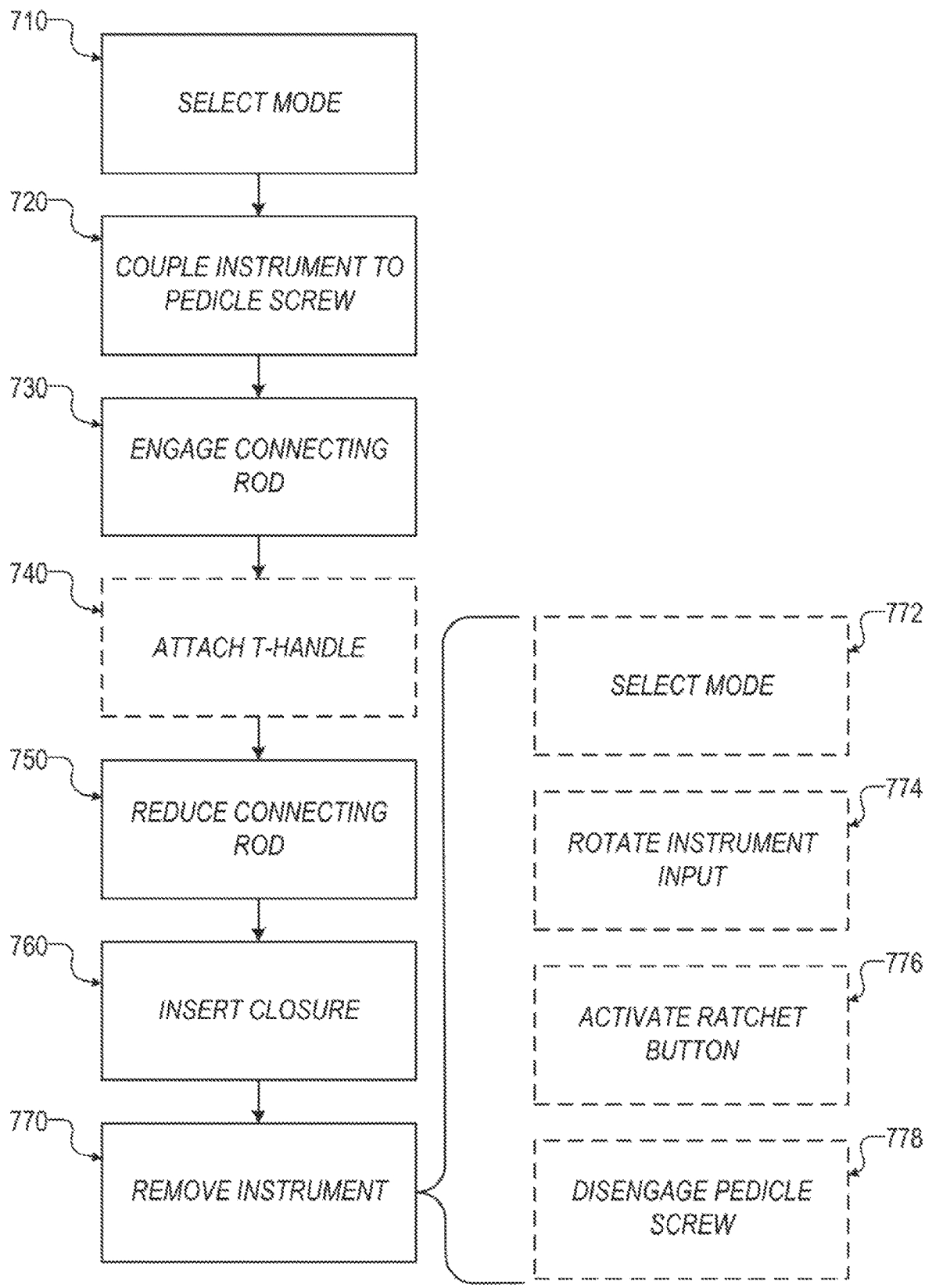
FIG. 7 is a flowchart illustrating a method for using a rod reduction instrument, in accordance an example embodiment.

FIG. 7 is a flowchart illustrating a method 700 for using a rod reduction instrument, such as rod reduction instrument 100 or 200 discussed above. The method 700 illustrates a common set of operations utilizing one of the rod reduction instruments discussed above. However, the method 700 does not cover all possible uses of the instruments, the operations discussed can be done in a different sequence, operations could be repeated or omitted, as fits the particular scenario of use. In this example, the method 700 can include operations such as: coupling to a pedicle screw at 710, selecting Quick On/Off mode at 720, sliding the outer housing into engage with a connecting rod at 730, optionally attaching a T-handle at 740, reducing the connecting rod at 750, insert closure into pedicle screw at 760, remove rod reduction instrument at 770.

The method 700 can begin at 710 the mode of operation of the instrument being selected. In this example, the Quick On/Off (or ratcheting) mode can be selected by shifting the slide lock, such as slide lock 132, into the Quick On/Off (distal) position. As discussed above, with the instrument in the Quick On/Off mode, the ratchet mechanism is free to ratchet. In other words, the engagement feature 141 of the lever member 140 is not fixed into engagement of the threaded proximal portion 102 of the inner sleeve 101. In another example, the user may choose to engage the threaded operation mode by shifting the slide lock into the Fixed (proximal) position. The operations discussed in method 700 are depicted in a common order of operation, but many of the operations can be shifted into other positions in the method or repeated. For example, the mode of operation can be switched at any point during the procedure.

At 720, the method 700 can continue by coupling the rod reduction instrument to a head of a pedicle screw. For example, engagement members 203 of the rod reduction instrument 100 can be placed into engagement with the head of a pedicle screw. Prior to engaging the pedicle screw, a ratchet release button 142 can be engaged and the inner shaft 101 fully extended into a fully open position. In an example, the instrument can include four separate engagement members that engage four vertical slots on the screw head. In other examples, the instrument may only include two engagement members that engage either arm of the U-shaped pedicle screw head.

Once the head of the pedicle screw is engaged, the method 700 can continue with the instrument free to engage the connecting rod at 730. In this example, the outer housing 110 can slide over the inner sleeve 201 to quickly engage the connecting rod through ratcheting. If the instrument were in the Fixed mode, rotational input to the top sleeve 115 would be necessary to translate the outer housing 110 over the inner sleeve 101 to engage the connecting rod.

With the connecting rod engaged, the method 700 can optionally continue at 740 with attachment of a T-handle on the tool socket 116 of the top sleeve 115. At 750, the method 700 can continue with the instrument being manipulated to reduce the connecting rod into the head of the pedicle screw. Instrument manipulation can include rotation of the T-handle (or top sleeve 115 if no extra torque is needed), which causes translation of the outer housing 110. Optionally, the instrument can be shifted into Fixed mode, if rod reduction is particular difficult to ensure that the ratchet mechanism 120 does not disengage during threaded reduction.

Once the rod is fully reduced into the pedicle screw, the method 700 can continue at 760 with a closure being inserted into the head of the pedicle screw to secure the rod in place. The instrument includes a central cylindrical passage to allow the closure to be inserted without removing the rod reduction instrument. Once the rod is secure, the method 700 can continue at 770 with removal of the reduction instrument from the head of the pedicle screw.

The instrument removal operation 770 can optionally include operations such as: selecting a mode at 772, rotating the instrument input at 774, activating the ratchet release button 776, and disengaging the pedicle screw at 778. In certain examples, the ratchet mechanism 120 in the Quick On/Off mode may not be able to release the tension on the rod reduction instrument 100. In such a scenario, the instrument can be shifted into Fixed mode through manipulation of the slide lock 132 into the proximal position. In fixed mode, the top sleeve 215 can be rotated at 774 to release tension on the outer housing 110 from engagement with the connecting rod. Once the tension is released, the mode can be shifted back to the Quick On/Off mode, and the ratchet release ratchet release button 142 can be activated at 776. Activating the ratchet release ratchet release button 142 allows the outer housing 110 to slide in reference to the inner sleeve 101 to open the instrument. Once the instrument is open, the engagement members 103 can be disengaged from the pedicle screw head at 778.

Various Notes & Examples

Each of these non-limiting examples may stand on its own, or may be combined in various permutations or combinations with one or more of the other examples.

Example 1 describes subject matter that can include a rod reduction instrument. In this example, the rod reduction instrument can include an inner shaft, an outer housing, and ratchet mechanism. The inner shaft can include a threaded proximal portion and a distal end, the distal end including a plurality of engagement members adapted to receive a housing of a pedicle screw. The outer housing can be slidably received over at least a portion of the inner shaft. The outer housing can also include a top sleeve and a bottom sleeve. In this example, the top sleeve can include the ratchet mechanism to selectively engage the threaded proximal portion of the inner shaft, and a distal end of the bottom sleeve adapted to engage a connecting rod. The ratchet mechanism can be disposed along the top sleeve of the outer housing. In this example, the ratchet mechanism can include an engagement feature to selectively engage the threaded proximal portion of the inner shaft, and a locking mechanism to selectively lock the engagement feature of the ratchet mechanism against the threaded proximal portion of the inner shaft.

In Example 2, the subject matter of Example 1 can optionally include the top sleeve being rotatably coupled to the bottom sleeve and adapted to translate rotational input into linear translation of the outer housing relative to the inner shaft.

In Example 3, the subject matter of Example 2 can optionally include the engagement feature of the ratchet mechanism engaging the threaded proximal portion of the inner shaft, upon receiving rotational input from the top sleeve, to linearly translate the outer shaft along a longitudinal axis in relation to the inner shaft.

In Example 4, the subject matter of any one of Examples 1 to 3 can optionally include the ratchet mechanism having a lever member including a proximal end and a distal end separated by a pivot.

In Example 5, the subject matter of Example 4 can optionally include the engagement feature of the proximal end of the lever member being adapted to selectively engage the threaded proximal portion of the inner shaft.

In Example 6, the subject matter of any one of Examples 4 and 5 can optionally include the distal end of the lever member having a button exposed on an external surface of the ratchet mechanism.

In Example 7, the subject matter of any one of Examples 4 to 6 can optionally include the pivot having a pivot shaft extending into opposing side walls of the locking mechanism, which enables rotational movement of the lever member about the pivot shaft.

In Example 8, the subject matter of Example 7 can optionally include the engagement feature on the proximal portion of the lever member selectively enaging the threaded proximal surface of the inner shaft through the rotational movement of the lever member.

In Example 9, the subject matter of Example 8 can optionally include the ratchet mechanism having a biasing member positioned against a superior surface of the proximal portion of the lever member opposite the engagement feature to bias the engagement feature against the threaded proximal surface of the inner shaft.

In Example 10, the subject matter of any one of Examples 4 to 9 can optionally include the locking mechanism having a slide lock disposed on an external surface of the ratchet mechanism adapted to lock the locking mechanism in a first position and unlock the locking mechanism in a second position.

In example 11, the subject matter of Example 10 can optionally include the slide lock being a U-shaped linear slide slidably engage along opposing sides of the ratchet mechanism, the slide lock translates along a longitudinal axis of the rod reduction instrument between the first position and the second position.

In Example 12, the subject matter of Example 11 can optionally include the slide lock including a transverse shaft projecting from an inferior surface of the slide lock towards the longitudinal axis to engage a locking surface on the lever member.

In Example 13, the subject matter of Example 12 can optionally include the slide lock being in the first position so the transverse shaft engages the locking surface to prevent the lever member from pivoting the engagement feature of the lever member away from the threaded proximal portion of the inner shaft.

In Example 14, the subject matter of Example 12 can optionally include the slide lock being in the second position so the inferior shaft is positioned over a cavity in the lever member allowing the lever member to pivot freely within the ratchet mechanism.

In Example 15, the subject matter of Example 10 can optionally include the slide lock being a stepped cylindrical shaft positioned transverse the lever member and disposed within a bore extending across a portion of a width of the ratchet mechanism.

In Example 16, the subject matter of Example 15 can optionally include the stepped cylindrical shaft including a large diameter section coupled to a small diameter section, the large diameter section engageable with a locking surface on the lever member to prevent pivoting of the lever member within the ratchet mechanism.

In Example 17, the subject matter of any one of Examples 15 or 16 can optionally include the slide lock translating within the bore between the first position and the second position.

In Example 18, the subject matter of Example 17 can optionally include the slide lock being in the first position where a portion of a larger diameter section of the stepped cylindrical shaft engages a locking surface on the lever member to lock-out the ratchet mechanism.

In Example 19, the subject matter of any one of Examples 15 to 18 can optionally include the locking mechanism including a biasing element disposed within the bore to bias the stepped cylindrical shaft into a particular position, such as the second position.

In Example 20, the subject matter of any one of Examples 15 to 19 can optionally include the stepped cylindrical shaft being biased into a second position where the lever member within the ratchet mechanism is free to pivot the engagement feature away from the threaded proximal portion of the inner shaft allowing the outer shaft to translate distally over the inner shaft towards the pedicle screw without rotational input.

In Example 21, the subject matter of any one of Examples 1 to 20 can optionally include the engagement feature being selected from a group of structures including: threads, numbs, cylindrical protrusions, square or rectangular protrusions, and one or more captured ball bearings.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rod reduction instrument comprising:
   an inner shaft including a threaded proximal portion and a distal end, the distal end including a plurality of engagement members adapted to receive a housing of a pedicle screw;
   an outer housing slidably received over at least a portion of the inner shaft, the outer housing including a top sleeve and a bottom sleeve, the top sleeve including a ratchet mechanism to selectively engage the threaded proximal portion of the inner shaft, and a distal end of the bottom sleeve adapted to engage a connecting rod;
   the ratchet mechanism disposed along the top sleeve of the outer housing, the ratchet mechanism including an engagement feature to selectively engage the threaded proximal portion of the inner shaft, the ratchet mechanism including a locking mechanism to selectively lock the engagement feature of the ratchet mechanism against the threaded proximal portion of the inner shaft,
   wherein the locking mechanism includes a slide lock disposed on an external surface of the ratchet mechanism and adapted to lock the locking mechanism in a first position and unlock the locking mechanism in a second position, and
   wherein the top sleeve is rotatably coupled to the bottom sleeve and adapted to translate rotational input into linear translation of the outer housing relative to the inner shaft.

2. The rod reduction instrument of claim 1, wherein the ratchet mechanism includes a lever member including a proximal end and a distal end separated by a pivot.

3. The rod reduction instrument of claim 2, wherein the proximal end of the lever member includes the engagement feature adapted to selectively engage the threaded proximal portion of the inner shaft.

4. The rod reduction instrument of claim 2, wherein the distal end of the lever member includes a button exposed on an external surface of the ratchet mechanism.

5. The rod reduction instrument of claim 2, wherein the pivot includes a pivot shaft extending into opposing side walls of the locking mechanism, and the pivot enables rotational movement of the lever member about the pivot shaft.

6. The rod reduction instrument of claim 5, wherein the rotational movement of the lever member enables the engagement feature on the proximal portion of the lever member to selectively engage the threaded proximal surface of the inner shaft.

7. The rod reduction instrument of claim 6, wherein the ratchet mechanism includes a biasing member positioned against a superior surface of the proximal portion of the member opposite the engagement feature to bias the engagement feature against the threaded proximal surface of the inner shaft.

8. The rod reduction instrument of claim 1, wherein the slide lock is a U-shaped linear slide slidably engage along opposing sides of the ratchet mechanism, the slide lock translates along a longitudinal axis of the rod reduction instrument between the first position and the second position.

9. The rod reduction instrument of claim 8, wherein the slide lock includes a transverse shaft projecting from an inferior surface of the slide lock towards the longitudinal axis to engage a locking surface on the lever member.

10. The rod reduction instrument of claim 9, wherein with the slide lock in the first position, the transverse shaft engages the locking surface to prevent the lever member from pivoting the engagement feature of the lever member away from the threaded proximal portion of the inner shaft.

11. The rod reduction instrument of claim 9, wherein with the slide lock in the second position the inferior shaft is positioned over a cavity in the lever member allowing the lever member to pivot freely within the ratchet mechanism.

12. The rod reduction instrument of claim 1, wherein the slide lock is a stepped cylindrical shaft positioned transverse the lever member and disposed within a bore extending across a portion of a width of the ratchet mechanism.

13. The rod reduction instrument of claim 12, wherein the stepped cylindrical shaft includes a large diameter section coupled to a small diameter section, the large diameter section engageable with a locking surface on the lever member to prevent pivoting of the lever member within the ratchet mechanism.

14. The rod reduction instrument of claim 12, wherein the slide lock translates within the bore between the first position and the second position.

15. The rod reduction instrument of claim 14, wherein with the slide lock in the first position a portion of a larger diameter section of the stepped cylindrical shaft engages a locking surface on the lever member to lock-out the ratchet mechanism.

16. The rod reduction instrument of claim 14, wherein the locking mechanism includes a biasing element disposed within the bore to bias the stepped cylindrical shaft into the second position.

17. The rod reduction instrument of claim 16, wherein when the stepped cylindrical shaft is biased into the second position the lever member within the ratchet mechanism is free to pivot the engagement feature away from the threaded proximal portion of the inner shaft allowing the outer shaft to translate distally over the inner shaft towards the pedicle screw without rotational input.

18. A rod reduction instrument comprising:
an inner shaft including a threaded proximal portion and a distal end, the distal end including a plurality of engagement members adapted to receive a housing of a pedicle screw;
an outer housing slidably received over at least a portion of the inner shaft, the outer housing including a top sleeve and a bottom sleeve, the bottom sleeve including a distal end adapted to engage a connecting rod;
a ratchet mechanism disposed along the top sleeve of the outer housing, the ratchet mechanism including an engagement feature to selectively engage the threaded proximal portion of the inner shaft, the ratchet mechanism including a locking mechanism including a slide lock disposed on an external surface of the ratchet mechanism, the slide lock including a first unlocked position and a second locked position to selectively lock the engagement feature of the ratchet mechanism against the threaded proximal portion of the inner shaft,
wherein the slide lock is a U-shaped linear slide slidably engage along opposing sides of the ratchet mechanism, the slide lock translates along a longitudinal axis of the rod reduction instrument between the first position and the second position.

19. A rod reduction instrument comprising:
an inner shaft including a threaded proximal portion and a distal end, the distal end including a plurality of engagement members adapted to receive a housing of a pedicle screw,
an outer housing slidably received over at least a portion of the inner shaft, the outer housing including a top sleeve and a bottom sleeve, the bottom sleeve including a distal end adapted to engage a connecting rod;
a ratchet mechanism disposed along the top sleeve of the outer housing, the ratchet mechanism including a threaded portion to selectively engage the threaded proximal portion of the inner shaft, the ratchet mechanism including a locking mechanism including a slide lock disposed on an external surface of the ratchet mechanism, the slide lock including a first unlocked position and a second locked position to selectively lock the threaded portion of the ratchet mechanism against the threaded proximal portion of the inner shaft,
wherein the slide lock is a stepped cylindrical shaft positioned transverse the lever member and disposed within a bore extending across a portion of a width of the ratchet mechanism.

20. A rod reduction instrument comprising:
an inner shaft including a threaded proximal portion and a distal end, the distal end including a plurality of engagement members adapted to receive a housing of a pedicle screw;
an outer housing slidably received over at least a portion of the inner shaft, the outer housing including a top sleeve and a bottom sleeve, the top sleeve including a ratchet mechanism to selectively engage the threaded proximal portion of the inner shaft, and a distal end of the bottom sleeve adapted to engage a connecting rod;
the ratchet mechanism disposed along the top sleeve of the outer housing, the ratchet mechanism including an engagement feature to selectively engage the threaded proximal portion of the inner shaft and a lever member including a proximal end and a distal end separated by a pivot, the ratchet mechanism further including a locking mechanism to selectively lock the engagement feature of the ratchet mechanism against the threaded proximal portion of the inner shaft, wherein the locking mechanism includes a slide lock disposed on an external surface of the ratchet mechanism and adapted to lock the locking mechanism in a first position and unlock the locking mechanism in a second position.

* * * * *

UNITED STATES PATENT AND TRADEMARK OFFICE
CERTIFICATE OF CORRECTION

Page 1 of 1

PATENT NO. : 10,918,424 B2
APPLICATION NO. : 16/295183
DATED : February 16, 2021
INVENTOR(S) : Stoll et al.

It is certified that error appears in the above-identified patent and that said Letters Patent is hereby corrected as shown below:

In the Claims

In Column 13, Line 13, in Claim 7, after "the", insert --lever--

In Column 14, Line 29, in Claim 19, delete "screw," and insert --screw;-- therefor Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*